United States Patent [19]
Latta et al.

[11] Patent Number: 6,033,885
[45] Date of Patent: Mar. 7, 2000

[54] INTEGRATIVE RECOMBINANT ADENOVIRUSES, PREPARATION THEREOF AND THERAPEUTICAL USES THEREOF

[75] Inventors: Martine Latta, Charenton le Pont; Patrice Denefle, Saint Maur; Emmanuelle Vigne, Ivry sur Seine; Michel Perricaudet, Ecrosnes, all of France

[73] Assignee: Rhone-Poulenc Rorer S.A., Antony Cedex, France

[21] Appl. No.: 08/702,573

[22] PCT Filed: Feb. 28, 1995

[86] PCT No.: PCT/FR95/00233

§ 371 Date: Sep. 12, 1996

§ 102(e) Date: Sep. 12, 1996

[87] PCT Pub. No.: WO95/23867

PCT Pub. Date: Sep. 8, 1995

[30]    Foreign Application Priority Data

Mar. 3, 1994 [FR] France ................................ 94 02445

[51] Int. Cl.[7] .............................. C12N 15/00; C12N 7/00; A01N 63/00; C12P 1/00
[52] U.S. Cl. ................. 435/172.3; 424/93.2; 435/320.1; 435/235.1; 435/70.3; 435/70.4; 435/41; 435/69.1; 435/69.3
[58] Field of Search .............................. 435/320.1, 235.1, 435/70.3, 70.4, 41, 69.1, 69.3, 172.3; 424/93.2

[56]    References Cited

FOREIGN PATENT DOCUMENTS

| 488 528 | 6/1992 | European Pat. Off. . |
| 592 836 | 4/1994 | European Pat. Off. . |
| WO93/09239 | 5/1993 | WIPO . |
| WO93/24641 | 12/1993 | WIPO . |

OTHER PUBLICATIONS

Rosenfeld, et al., In Vivo Transfer of the Human Cystic Fibrosis Transmembrane Conductance Regulator Gene to the Airway Epithelium, Cell, vol. 68, 143–155, see p. 143, col. 1, "Summary" and col. 2, second paragraph, "Introduction", and p. 144, Res, Jan. 1992.

Walsh C. et al. Regulated high level expression of a human gamma–globin gene introduced into erythroid cells by an adeno–associated virus vector, Proc. Nat'l Acad. Sci. 89:7257–7261, Aug. 1992.

Flotte T. et al. Expression of the cystic fibrosis transmembrane conductance regulator from a novel adeno–associated virus promoter, Jol. Biol. Chem. 268(5):3781–3790, Feb. 1993.

Nahreini et al., Cloning and integration of DNA fragments in human cells via the inverted terminal repeats of the adeno–associated virus 2 genome, Gene 119, 265–272 (1992).

*Primary Examiner*—Jeffrey Stucker
*Assistant Examiner*—Honkyel Park

[57]    ABSTRACT

The present invention relates to recombinant adenoviruses having a cassette capable of integrating into the genome of infected cells, their preparation, pharmaceutical compositions containing them, and their use. In particular, the cassette contains at least one inverted terminal repeat (ITR) Sequence from AAV and a heterologous DNA Sequence.

31 Claims, 9 Drawing Sheets

SEQUENCE LISTING (1) GENERAL INFORMATION:

(iii) NUMBER OF SEQUENCES: 13

(2) INFORMATION FOR SEQ ID NO:1:

(i) SEQUENCE CHARACTERISTICS:
       (A) LENGTH: 135 base pairs
       (B) TYPE: nucleic acid
       (C) STRANDEDNESS: double
       (D) TOPOLOGY: linear (ii) MOLECULE TYPE: other nucleic acid (ix) FEATURE:
       (A) NAME/KEY: misc_feature
       (B) LOCATION: 1..135
       (D) OTHER INFORMATION: /note= "Right ITR Sequence in
           pXL2373"

(xi) SEQUENCE DESCRIPTION: SEQ ID NO:1:

```
CCATGGCTAC GTAGATAAGT AGCATGGCGG GTTAATCATT AACTACAAGG AACCCCTAGT      60

GATGGAGTTG GCCACTCCCT CTCTGCGCGC TCGCTCGCTC ACTGAGGCCG GGCGACCAAA     120

GGTCGCCCGA CGCCC                                                      135
```

(2) INFORMATION FOR SEQ ID NO:2:

(i) SEQUENCE CHARACTERISTICS:
       (A) LENGTH: 174 base pairs
       (B) TYPE: nucleic acid
       (C) STRANDEDNESS: double
       (D) TOPOLOGY: linear (ii) MOLECULE TYPE: other nucleic acid (ix) FEATURE:
       (A) NAME/KEY: misc_feature
       (B) LOCATION: 1..174
       (D) OTHER INFORMATION: /note= "Left ITR Sequence in
           pXL2384 and pXL2373"

(xi) SEQUENCE DESCRIPTION: SEQ ID NO:2:

```
GCGCGCTCGC TCGCTCACTG AGGCCGCCCG GGCAAAGCCC GGGCGTCGGG CGACCTTTGG      60

TCGCCCGGCC TCAGTGAGCG AGCGAGCGCG CAGAGAGGGA GTGGCCAACT CCATCACTAG     120

GGGTTCCTTG TAGTTAATGA TTAACCCGCC ATGCTACTTA TCTACGTAGC CATG           174
```

(2) INFORMATION FOR SEQ ID NO:3:

(i) SEQUENCE CHARACTERISTICS:
       (A) LENGTH: 192 base pairs
       (B) TYPE: nucleic acid
       (C) STRANDEDNESS: double
       (D) TOPOLOGY: linear (ii) MOLECULE TYPE: other nucleic acid (ix) FEATURE:
       (A) NAME/KEY: misc_feature
       (B) LOCATION: 1..192
       (D) OTHER INFORMATION: /note= "Right ITR Sequence in
           pXL2384"

(xi) SEQUENCE DESCRIPTION: SEQ ID NO:3:

```
CCATGGCTAC GTAGATAAGT AGCATGGCGG GTTAATCATT AACTACAAGG AACCCCTAGT      60

GATGGAGTTG GCCACTCCCT CTCTGCGCGC TCGCTCGCTC ACTGAGGCCG GGCGACCAAA     120
```

GGTCGCCCGA CGCCCGGGCT TTGCCCGGGC GGCCTCAGTG AGCGAGCGAG CGCGCAGAGA    180

GGGAGTGGCC AA    192

(2) INFORMATION FOR SEQ ID NO:4:

(i) SEQUENCE CHARACTERISTICS:
        (A) LENGTH: 145 base pairs
        (B) TYPE: nucleic acid
        (C) STRANDEDNESS: double
        (D) TOPOLOGY: linear (ii) MOLECULE TYPE: other nucleic acid (ix) FEATURE:
        (A) NAME/KEY: misc_feature
        (B) LOCATION: 1..145
        (D) OTHER INFORMATION: /note= "Minimal ITR Sequence"

(xi) SEQUENCE DESCRIPTION: SEQ ID NO:4:

TTGGCCACTC CCTCTCTGCG CGCTCGCTCG CTCACTGAGG CCGGGCGACC AAAGGTCGCC    60

CGACGCCCGG GCTTTGCCCG GCGGCCTCA GTGAGCGAGC GAGCGCGCAG AGAGGGAGTG    120

GCCAACTCCA TCACTAGGGG TTCCT    145

(2) INFORMATION FOR SEQ ID NO:5:

(i) SEQUENCE CHARACTERISTICS:
        (A) LENGTH: 194 base pairs
        (B) TYPE: nucleic acid
        (C) STRANDEDNESS: double
        (D) TOPOLOGY: linear (ii) MOLECULE TYPE: other nucleic acid (ix) FEATURE:
        (A) NAME/KEY: misc_feature
        (B) LOCATION: 1..194
        (D) OTHER INFORMATION: /note= "Left AAV ITR From pXL2629"

(xi) SEQUENCE DESCRIPTION: SEQ ID NO:5:

AGATCTGGGC CACTCCCTCT CTGCGCGCTC GCTCGCTCAC TGAGGCCGGG CGACCAAAGG    60

TCGCCCGACG CCCGGGCTTT GCCCGGGCGG CCTCAGTGAG CGAGCGAGCG CGCAGAGAGG    120

GAGTGGCAAC TCCATCACTA GGGGTTCCTG GAGGGGTGGA GGGGGGATCC ACTAGTTCTA    180

GAACTAGTGG ATCC    194

(2) INFORMATION FOR SEQ ID NO:6:

(i) SEQUENCE CHARACTERISTICS:
        (A) LENGTH: 73 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO:6:

CTAGATTGGC CACTCCCTCT CTGCGCGCTC GCTCGCTCAC TGAGGCCGGG CGACCAAAGG    60

TCGCCCGACG CCA    73

(2) INFORMATION FOR SEQ ID NO:7:

(i) SEQUENCE CHARACTERISTICS:
        (A) LENGTH: 73 base pairs
        (B) TYPE: nucleic acid (C) STRANDEDNESS: double
            (D) TOPOLOGY: linear (ii) MOLECULE TYPE: other nucleic acid
            (A) DESCRIPTION: /desc = "oligonucleotide"

(xi) SEQUENCE DESCRIPTION: SEQ ID NO:7:

AGCTTGGCGT CGGGCGACCT TTGGTCGCCC GGCCTCAGTG AGCGAGCGAG CGCGCAGAGA       60

GGGAGTGGCC AAT       73

(2) INFORMATION FOR SEQ ID NO:8:

(i) SEQUENCE CHARACTERISTICS:
            (A) LENGTH: 46 base pairs
            (B) TYPE: nucleic acid
            (C) STRANDEDNESS: double
            (D) TOPOLOGY: linear (ii) MOLECULE TYPE: other nucleic acid
            (A) DESCRIPTION: /desc = "oligonucleotide"

(xi) SEQUENCE DESCRIPTION: SEQ ID NO:8:

AGCTTGACGC CCGGGCTTTG CCCGGGCGGC CTCAGTGAGC GAGCGA       46

(2) INFORMATION FOR SEQ ID NO:9:

(i) SEQUENCE CHARACTERISTICS:
            (A) LENGTH: 48 base pairs
            (B) TYPE: nucleic acid
            (C) STRANDEDNESS: double
            (D) TOPOLOGY: linear (ii) MOLECULE TYPE: other nucleic acid
            (A) DESCRIPTION: /desc = "oligonucleotide"

(xi) SEQUENCE DESCRIPTION: SEQ ID NO:9:

GCGCGCTCGC TCGCTCACTG AGGCCGCCCG GGCAAAGCCC GGGCGTCA       48

(2) INFORMATION FOR SEQ ID NO:10:

(i) SEQUENCE CHARACTERISTICS:
            (A) LENGTH: 50 base pairs
            (B) TYPE: nucleic acid
            (C) STRANDEDNESS: double
            (D) TOPOLOGY: linear (ii) MOLECULE TYPE: other nucleic acid
            (A) DESCRIPTION: /desc = "oligonucleotide"

(xi) SEQUENCE DESCRIPTION: SEQ ID NO:10:

GCGCGCAGAG AGGGAGTGGC CAACTCCATC ACTAGGGGTT CCTACTAGTG       50

(2) INFORMATION FOR SEQ ID NO:11:

(i) SEQUENCE CHARACTERISTICS:
            (A) LENGTH: 48 base pairs
            (B) TYPE: nucleic acid
            (C) STRANDEDNESS: double
            (D) TOPOLOGY: linear (ii) MOLECULE TYPE: other nucleic acid
            (A) DESCRIPTION: /desc = "oligonucleotide"

(xi) SEQUENCE DESCRIPTION: SEQ ID NO:11:

GATCCACTAG TAGGAACCCC TAGTGATGGA GTTGGCCACT CCCTCTCT       48

(2) INFORMATION FOR SEQ ID NO:12:

```
    (i) SEQUENCE CHARACTERISTICS:
        (A) LENGTH: 12 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO:12:

GATCTTTCGA AT                                                              12

(2) INFORMATION FOR SEQ ID NO:13:

(i) SEQUENCE CHARACTERISTICS:
        (A) LENGTH: 12 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO:13:

CTAGATTCGA AA                                                              12
```

INTEGRATIVE RECOMBINANT ADENOVIRUSES, PREPARATION THEREOF AND THERAPEUTICAL USES THEREOF

BACKGROUND OF THE INVENTION

The present invention relates to recombinant vectors of viral origin and their therapeutic use. More particularly, it relates to recombinant adenoviruses containing a cassette capable of becoming integrated into the genome of the infected cells. The invention also relates to the preparation of these vectors, the pharmaceutical compositions containing them and their use for the transfer of genes in vitro, ex vivo and in vivo, especially within the framework of gene and cell therapies.

Gene and cell therapy consists in correcting a deficiency or an abnormality (mutation, aberrant expression and the like) or in ensuring the expression of a protein of therapeutic interest by the introduction of a genetic information into the cell or the affected organ. This genetic information can be introduced either in vitro into a cell extracted from the organ, the modified cell then being reintroduced into the body, or directly in vivo into the appropriate tissue. Various techniques have been described for the transfer of this genetic information, amongst which are various transfection techniques involving complexes of DNA and DEAE-dextran (Pagano et al., J. Virol. 1 (1967) 891), of DNA and nuclear proteins (Kaneda et al., Science 243 (1989) 375), of DNA and lipids (Felgner et al., PNAS 84 (1987) 7413), of DNA and polylysine, the use of liposomes (Fraley et al., J. Biol. Chem. 255 (1980) 10431) and the like.

More recently, the use of viruses as vectors for the transfer of genes appeared as a promising alternative to these physicochemical transfection techniques. In this respect, various viruses have been tested for their capacity to infect certain cell populations, in particular retroviruses (RSV, HMS, MMS and the like), HSV virus, adeno-associated viruses, and adenoviruses. However, the viral vectors developed up until now do not make it possible to solve satisfactorily all the difficulties linked to the transfer of genes into the cells and/or the body. Thus, adenovirus, which possesses attractive properties for the transfer of genes (possibility of producing high titres, low pathogenicity) is an extrachromosomal virus. Because of this, in dividing cells, the recombinant virus is diluted over generations and eventually disappears completely from the daughter cells. On the other hand, whereas retroviral vectors or vectors derived from adeno-associated viruses (AAV) are capable of becoming integrated into the genome of the cells which they infect, they cannot be produced in large quantities nor for example incorporate large transgenes.

BRIEF SUMMARY OF THE INVENTION

The present invention provides an advantageous solution to these problems. The present invention resides indeed in the development of recombinant vectors which can be used in gene therapy, possessing the infecting properties of a recombinant adenovirus vector and permitting the integration of a heterologous sequence into the genome of the infected cell or organ.

A first subject of the invention relates more particularly to a defective recombinant adenovirus comprising a cassette capable of becoming integrated into the genome of the infected cells.

Generally, the cassette comprises a desired DNA sequence, which is most often heterologous in relation to the adenovirus, and elements permitting its integration into the genome of the infected cells. Advantageously, the elements permitting the integration are of viral origin. Thus, the vectors of the invention combine properties of two types of viruses: the adenoviruses and the integrative viruses.

The vectors of the invention are particularly advantageous since they can be produced at high titres, are not pathogenic, possess a broad host spectrum, are capable of incorporating large heterologous DNA sequences and of integrating the said sequences into the genome of the infected cells.

Furthermore, the vectors of the invention make it possible to limit the risks of dissemination of the DNA sequence which it is desired to transfer to the cell or the body. Once the said cell has been integrated into the genome, it can no longer be excised and incorporated into an infectious viral particle.

In addition, the vectors of the invention make it possible, advantageously, to transfer to the cells a DNA sequence completely free of viral genes. Indeed, the cassette permitting the integration into the genome can be completely free of any coding sequence of viral origin. The only viral regions which can be introduced are the elements for integration.

Moreover, depending on the construct used, the vectors of the invention allow integration of the heterologous DNA sequence at a precise site of the genome of the infected cell, and without cytotoxicity.

Preferably, the elements permitting the integration of the cassette consist of one or more inverted terminal repeat sequences. Yet more preferably, the elements permitting the integration of the cassette consist of one or more inverted terminal repeat sequences of an adeno-associated virus (AAV).

A preferred subject of the invention therefore relates to a defective recombinant adenovirus comprising a cassette containing at least one AAV inverted terminal repeat sequence and one heterologous DNA sequence.

The Applicant has indeed shown, in a particularly advantageous manner, that it is possible to use the integrating properties of AAV (adeno-associated virus) to construct a viral vector according to the invention, as defined above.

AAVs, like adenoviruses, are benign pathogenic viruses of the aerial pathways. In the absence of helper virus, AAVs possess the property of becoming stably integrated, in the form of a provirus, into a preferred site of the genome of human cells (region of chromosome 19). The genome of AAVs has been cloned, sequenced and characterized. It comprises about 4700 bases and contains, at each end, an inverted terminal repeat region (ITR) of 145 bases approximately. The remainder of the genome is divided into 2 essential regions carrying the encapsulation functions: the left-hand part of the genome, which contains the rep gene involved in viral replication and the expression of the viral genes; the right-hand part of the genome, which contains the cap gene encoding the virus capsid proteins.

The inverted terminal repeat regions (ITR) of AAVs serve as replication origin for the virus and are also responsible for the integration of the virus into the genome of the infected cells. It has now been shown that it is possible to introduce one or more of these ITRs into a recombinant adenovirus so as to target the integration of a heterologous DNA sequence onto the chromosome of a target cell, and thus enhance the stability of expression over time. The Applicant has indeed shown that these sequences can be introduced into the genome of an adenovirus, that they conserve their functionality in an adenoviral context and that they can be used in gene or cell therapy to stably integrate into human cells a sequence introduced via an adenovirus. Furthermore, these hybrid viruses of the invention can be prepared at titres comparable to those of the adenovirus (much higher than those obtained with the AAV), permitting multiple therapeutic applications.

In a first embodiment, the integrating cassette according to the invention contains only one AAV ITR, linked to the heterologous DNA sequence. It has indeed been shown that a single AAV ITR is sufficient to induce the integration of the heterologous sequence. In this embodiment, the ITR may be located downstream or upstream of the heterologous DNA sequence (FIGS. 1a and 1b).

Advantageously, the adenovirus according to the invention comprises a cassette containing at least one heterologous DNA sequence bordered by two AAV ITRs (FIG. 1c). This embodiment is particularly advantageous since the integration efficiency is very high.

As indicated above, the AAV genome comprises 2 ITRs located at its 2 ends: one 5' ITR located at the left end, and one 3' ITR located at the right end. The sequence of these ITRs is identical, and they are orientated in the opposite direction relative to one another. Moreover, in some cases, the structure of the ITRs can be modified by rearrangements, but the base composition is not altered. For the preparation of the vectors of the invention, it is possible to use any one or more of these ITRs.

In a particularly advantageous embodiment of the invention, the cassette comprises a heterologous DNA sequence bordered by an AAV 5' ITR and 3' ITR.

The AAV ITRs can be obtained in various ways. They can first be isolated from the genome of an AAV, by conventional molecular biology techniques (see especially WO91/18088, WO93/09239). As indicated above, these sequences possess about 145 bp, are located at the ends of the AAV genome and can be excised by means of appropriate restriction enzymes. In this respect, they can be isolated from the various AAV serotypes, such as especially AAV1, AAV2, AAV3 and AAV4. Moreover, the sequence of the ITRs being known, they can also be synthesized artificially by means of nucleic acid synthesizers, or obtained by mixed techniques (isolation from the genome, then extension by synthesis techniques). Finally, these ITRs can also be modified by any technique known to persons skilled in the art (molecular biology, chemistry, enzymology and the like), with the aim of enhancing their functionality, of reducing their size, of increasing their stability after integration or their integration specificity and the like. In particular, they can be modified by mutation, deletion and/or addition of base pairs, according to conventional molecular biology techniques.

Advantageously, in the adenoviruses of the invention, the ITR(s) used are AAV-2 ITRs.

The ITRs used in the present invention may comprise only the sequences necessary and sufficient for the integration into the genome of the cells (strict ITR). As regards the AAVs, the strict ITRs correspond to the 145 bp situated on either side of the genome (SEQ ID No. 4). However, the ITRs used may also comprise additional sequences, for example adjacent sequences of the AAV genome, and/or deletions, insofar as these sequences and/or deletions do not suppress the integrating capacity of the cassette. Thus, they can be isolated in the form of longer fragments (for example up to 1000 bp), which can be used as such, if they do not suppress the integrating capacity of the cassette, or digested beforehand in order to reduce their size (see for example SEQ ID No. 1–3+5).

To determine if the sequence(s) chosen can permit integration into the chromosome, it is for example possible to transfect a human cell line (for example Hela or 293), on the one hand, with a plasmid carrying a neoR type selectable gene between the sequences to be tested or beside the sequence to be tested and, on the other hand, with a control plasmid carrying the same selectable gene without the said sequences, to select clones by adding the antibiotic G418, then to compare, between both types of transfections, the number of clones obtained. The integration frequency obtained with the test sequence(s) should be greater than that obtained by mere selection, for the said sequences to be usable.

Another way of testing the integrating capacity of the sequences is to transfect the same line, on the one hand, with a plasmid carrying a marker gene (ex. βgal) between the sequences to be tested and, on the other hand, with a control plasmid carrying the same marker gene without the said sequences, and to compare, during the course of the passages, the enzymatic activity between the two transfections; it being necessary for the activity to decrease exponentially in the control transfections and to remain more stable in the other. In this respect, the "integrant" cells expressing βgal can be located, after fixing, by Xgal staining.

Whichever ITR sequence is used, it is particularly advantageous that it is free of coding viral sequence. Indeed, this makes it possible to avoid introducing into the genome of the cells viral regions capable of encoding all or part of the viral messengers or proteins which are potentially toxic or immunogenic.

For the preparation of the vectors of the invention, it is therefore particularly preferred to use one or more ITRs free of coding viral sequence.

In the cassettes of the invention, the heterologous DNA sequence and the ITR(s) should be arranged so as to permit the integration of the cassette into the genome of the infected cell. They can be either directly joined, or separated by sequences which do not alter the integrating property of the cassette. In particular, this may be one or more restriction sites, regions derived from a plasmid used during the construction (example: bacterial plasmid), or any neutral region and the like.

As indicated above, the adenoviruses of the invention contain a cassette permitting the integration of a heterologous DNA sequence into the genome of the infected cell. The heterologous DNA sequence may be any sequence whose transfer into a cell or an organism is desired.

Advantageously, the heterologous DNA sequence contains a therapeutic gene. For the purposes of the invention, therapeutic gene is understood to mean in particular any gene encoding a protein product having a therapeutic effect. The protein product thus encoded may be a protein, peptide and the like. This protein product may be homologous with respect to the target cell (that is to say a product which is normally expressed in the target cell when the latter does not have any disease). In this case, the expression of a protein makes it possible for example to palliate an insufficient expression in the cell or the expression of an inactive or weakly active protein because of a modification, or alternatively to overexpress the said protein. The therapeutic gene may also encode a mutant of a cellular protein, having an enhanced stability, a modified activity and the like. The protein product may also be heterologous with respect to the target cell. In this case, an expressed protein may for example complement or provide a deficient activity in the cell, allowing it to combat a disease, or to stimulate an immune response.

Among the therapeutic products for the purposes of the present invention, there may be mentioned more particularly enzymes, blood derivatives, hormones, lymphokines: interleukins, interferons, TNF, and the like (FR 9203120), growth factors (erythropoietin, G-CSF, M-CSF, GM-CSF, and the like), neurotransmitters or their precursors or synthetic enzymes, trophic factors: BDNF, CNTF, NGF, IGF, GMF, aFGF, bFGF, NT3, NT5, HARP/pleiotrophin, and the like; apolipoproteins: ApoAI, ApoAIV, ApoE, and the like (FR 93 05125), dystrophin or a minidystrophin (FR 9111947), the protein CFTR associated with cystic fibrosis, tumour suppressor genes: p53, Rb, RaplA, DCC, k-rev, and the like (FR 93 04745), genes encoding factors involved in coagulation: factors VII, VIII, IX, the genes involved in DNA repair, suicide genes (thymidine kinase, cytosine deaminase) and the like.

The therapeutic gene may also be a gene or an antisense sequence whose expression in the target cell makes it possible to control the expression of genes or the transcription of cellular mRNAs. Such sequences can, for example, be transcribed in the target cell into RNAs complementary to cellular mRNAs and thus block their translation into protein, according to the technique described in Patent EP 140 308. The antisenses also comprise the sequences encoding ribozymes, which are capable of selectively destroying target RNAs (EP 321 201).

The therapeutic gene may also contain one or more sequences encoding an antigenic peptide capable of generating an immune response in man or in animals. In this specific embodiment of the invention, the recombinant adenoviruses can be used either for the preparation of vaccines or for carrying out immunotherapeutic treatments applied to man or to animals, especially against microorganisms, viruses or cancers. This may be especially antigenic peptides specific for the Epstein Barr virus, the HIV virus, the hepatitis B virus (EP 185 573), the pseudorabies virus or alternatively specific for tumours (EP 259 212).

In addition, advantageously, the heterologous DNA sequence may contain in addition to the therapeutic gene, a marker gene such as for example the β-galactosidase gene or the neo gene. The adenoviruses of the invention in which the cassette contains two genes (a therapeutic gene and a marker gene in particular) are particularly valuable because their construction is greatly facilitated.

Preferably, the heterologous DNA sequence also comprises sequences permitting the expression of the therapeutic gene in the cell or desired organ. This may be the sequences which are naturally responsible for the expression of the considered gene when these sequences are capable of functioning in the infected cell. This may also be sequences of different origin (which are responsible for the expression of other proteins, or which are even synthetic). In particular, this may be promoter sequences of eucaryotic or viral genes. For example, this may be promoter sequences derived from the genome of the cell which it is desired to infect. Likewise, this may be promoter sequences derived from the genome of a virus. In this respect, there may be mentioned for example the promoters of the E1A, MLP, CMV, LTR-RSV genes and the like. In addition, these expression sequences can be modified by the addition of activating sequences, regulatory sequences or sequences conferring on the gene of interest a tissue expression specificity.

Moreover, the heterologous DNA sequence may also contain a signal sequence directing the therapeutic product synthesized in the secretion pathways of the target cell. This signal sequence may be the natural signal sequence of the therapeutic product, but it may also be any other functional signal sequence or an artificial signal sequence.

The defective recombinant adenoviruses according to the invention are adenoviruses which are incapable of autonomously replicating in the target cell. Generally, the genome of the defective adenoviruses used within the framework of the present invention is therefore free of at least the sequences necessary for the replication of the said virus in the infected cell. These regions can be either removed (completely or partly), or rendered non-functional, or substituted by other sequences and especially by the cassette. Preferably, the defective virus nevertheless conserves the sequences of its genome which are necessary for the encapsulation of the viral particles.

There are various adenovirus serotypes whose structure and properties vary somewhat. Among these serotypes, the use, within the framework of the present invention, of the type 2 or 5 human adenoviruses (Ad 2 or Ad 5) or the adenoviruses of animal origin (see Application WO94/26914) is preferred. Among the adenoviruses of animal origin which can be used within the framework of the present invention, there may be mentioned adenoviruses of canine, bovine, murine (example: Mav1, Beard et al., Virology 75 (1990) 81), ovine, porcine, avian or alternatively simian (example: SAV) origin. Preferably, the adenovirus of animal origin is a canine adenovirus, more preferably a CAV2 adenovirus [Manhattan or A26/61 strain (ATCC VR-800) for example].

Preferably, adenoviruses of human or canine or mixed origin are used within the framework of the invention.

The defective recombinant adenoviruses according to the invention can be prepared by any technique known to persons skilled in the art (Levrero et al., Gene 101 (1991) 195, EP 185 573; Graham, EMBO J. 3 (1984) 2917). In particular, they can be prepared by homologous recombination between an adenovirus and a plasmid carrying, inter alia, the cassette. The homologous recombination occurs after cotransfection of the said adenovirus and plasmid into an appropriate cell line. The cell line used should preferably (i) be transformable by the said elements, and (ii) contain the sequences capable of complementing the defective adenovirus genome part, preferably in integrated form in order to avoid risks of recombination. As an example of a cell line, there may be mentioned the human embryonic kidney line 293 (Graham et al., J. Gen. Virol. 36 (1977) 59) which contains especially, integrated into its genome, the left-hand part of the genome of an Ad5 adenovirus (12%). Strategies for constructing vectors derived from adenoviruses have also been described in applications Nos. WO94/26914 and FR 2,707,664, which are incorporated into the present application by reference.

Then the adenoviruses which have multiplied are recovered and purified according to conventional molecular biology techniques, as illustrated in the examples.

The recombinant adenoviruses prepared according to the present invention can be used for the transfer of genes of interest in vitro, ex vivo or in vivo. In vitro, they can make it possible to transfer a gene to a cell line, for example so as to produce a recombinant protein. Ex vivo, they can be used to transfer a gene over a population of cells collected from an organism, optionally selected and amplified, with the aim of conferring on these cells properties desired for their readministration to an organism. In vivo, they can be used to transfer genes by direct administration of a purified solution, optionally combined with one or more pharmaceutical vehicles.

In this respect, the present invention also relates to any pharmaceutical composition comprising one or more defective recombinant adenoviruses as described above. These pharmaceutical compositions can be formulated for topical, oral, parenteral, intranasal, intravenous, intramuscular, subcutaneous, intraocular or transdermal administration and the like. Preferably, the pharmaceutical compositions of the invention contain a vehicle which is pharmaceutically acceptable for an injectable formulation. This may be in particular isotonic sterile solutions, or dry, especially freeze-dried, compositions which, upon addition, depending on the case, of sterilized water or physiological saline, permit the preparation of injectable solutions.

The doses of defective recombinant adenovirus used for the injection can be adjusted according to various parameters, especially according to the mode of administration used, the pathology concerned, the gene to be expressed, or alternatively the duration of treatment desired. Generally, the recombinant adenoviruses according to the invention are formulated and administered in the form of doses of between $10^4$ and $10^{14}$ pfu/ml, and preferably $10^6$ to $10^{10}$ pfu/ml. The term pfu (plaque forming unit) corresponds to the infectivity of a virus solution, and is determined by infection of an appropriate cell culture, and measurement, generally after 48 hours, of the number of plaques of infected cells. The techniques for determining the pfu titre of a viral solution are well documented in the literature.

The present invention thus offers a very effective means for transferring genes into cells. The vectors of the invention can be used in numerous applications, such as genetic diseases (myopathy, cystic fibrosis, SCID and the like), pathologies of the central nervous system (Alzheimer, Parkinson and the like), cardiovascular diseases (haemophilia, atherosclerosis), AIDS, cancers and the like.

The vectors of the invention are most particularly advantageous for the transfer of genes into dividing cells. Indeed, by virtue of the infecting capacities of the adenoviral vector and the integrating properties of the cassette, the vectors of the invention make it possible to confer on dividing cells properties which are stable over generations. Preferred examples of these types of cells are especially haematopoietic cells (stem cells, progenitors and the like), and cancer cells. Most particularly, the vectors of the invention can be used for the transfer of genes into CD34 cells.

In this respect, the invention also relates to any mammalian cell modified by an adenovirus as described above. More preferably, this is a human cell, and still more preferably, chosen from haematopoietic, especially CD34, or tumour cells.

In addition, the vectors of the invention can be used to modify both human and animal cells (ovines, bovines, domestic animals (dogs, cats and the like), horses, fish and the like).

The invention thus provides a particularly effective method for the administration of genes in vivo, comprising the administration of a vector as defined above, comprising a cassette composed of the said gene and of elements permitting its integration into the genome of all or part of the infected cells.

The adenoviruses of the invention, comprising a cassette consisting of a heterologous DNA sequence bordered by 2 AAV ITRs, can also be used for the production of recombinant AAVs. The AAVs indeed require, in order to replicate, the presence of a helper virus. This may be in particular an adenovirus, a herpes virus or a vaccinia virus. In the absence of such a helper virus, the AAVs remain in latent form in the genome of the infected cells, but cannot replicate. For this reason, recombinant AAVs are generally produced by cotransfection into a cell line infected with the helper virus (especially adenovirus) of a plasmid carrying the AAV cassette (gene bordered by ITRs) and a plasmid carrying the encapsulation genes (rep/cap plasmid). This process involves three partners: the helper virus, the AAV plasmid and the rep/cap plasmid. By virtue of the present invention, this process can be simplified to 2 partners. Indeed, the adenoviruses of the invention play both the role of helper virus and AAV plasmid. Thus, another application of the invention consists in a process for preparing recombinant AAVs according to which the producing cells are infected with an adenovirus as described above and transfected with a plasmid carrying the rep and cap genes. According to a variant of this process, the rep and cap genes are also carried by a virus (especially an adenovirus) used to coinfect the producing cells. This variant is even more advantageous since it makes it possible to replace the step for transfection of the rep/cap plasmid by an infection with a rep/cap virus, which is much more efficient. Still according to a preferred variant embodiment, the process of the invention requires a producing line containing, integrated into its genome, the rep and cap genes. In this variant, a single step for infection with the virus of the invention is sufficient. It is also possible to use a virus according to the invention containing, in addition to the heterologous DNA/AAV ITR cassette, a cassette for expressing the rep and cap genes. According to this embodiment, the rep and cap genes can be placed under the control of a strong and/or inducible promoter. Advantageously, the adenovirus is deleted of the entire viral genes except the E4 region, and it is coinfected with another adenovirus carrying the entire genome except the E4 region, into cells 293. This embodiment is particularly advantageous. Indeed, the E4 virus used is the same for all the heterologous DNAs. Furthermore, the construction of the virus involves a plasmid carrying E4, the PSI sequence and the ITRs of the adenovirus (plasmid pE4ITR, cf FR 2,707, 664), which can be easily manipulated, into which are introduced the rep and cap genes and the heterologous DNA flanked by the AAV ITRs. This strategy thus makes it possible to propagate the 2 viruses to all the cells, contrary to the transfection of a rep/cap plasmid which involves only a fraction of the cell population and therefore only gives AAV titles which are not very high.

The present invention will be more fully described with the aid of the following examples which should be considered as illustrative and non-limiting.

BRIEF DESCRIPTION OF THE DRAWINGS

FIG. 1: Schematic representation of the cassettes according to the invention

DETAILED DESCRIPTION OF THE INVENTION

General Molecular Biology Techniques

Figures 1A, 1B, 1C, 2:
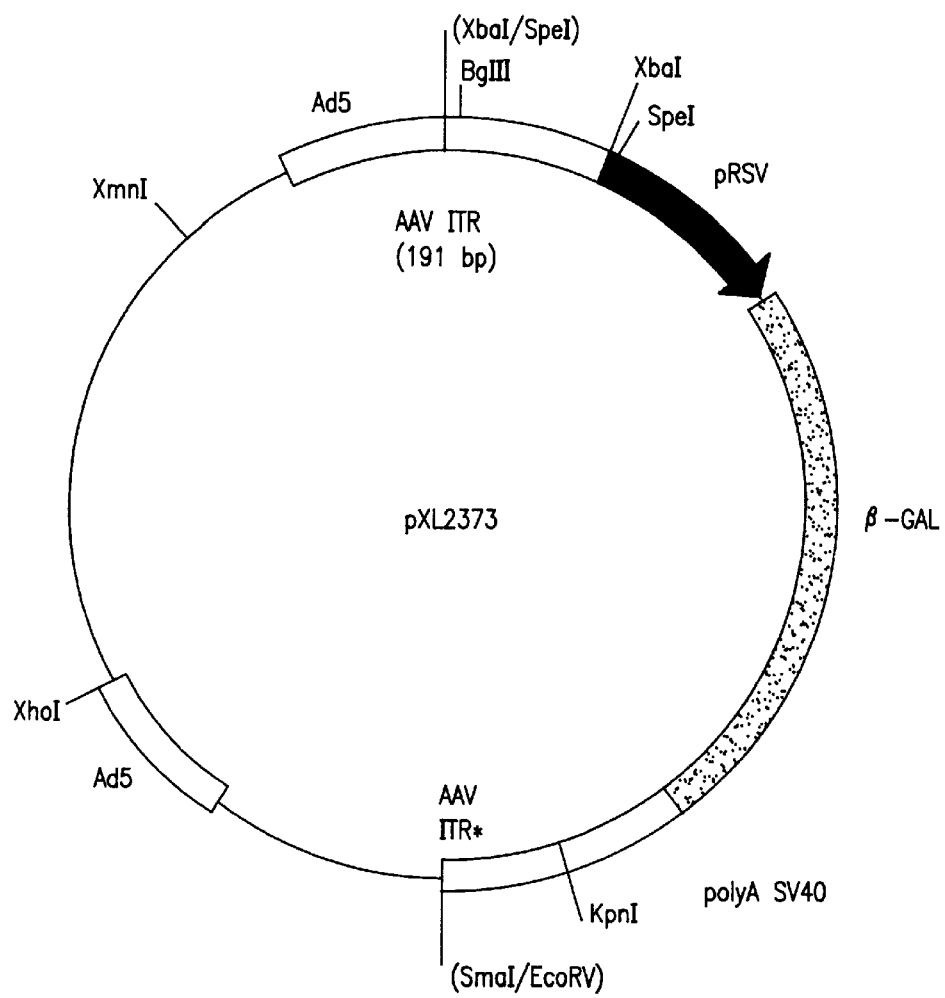
FIG. 2: Representation of the vector pXL2373

The methods conventionally used in molecular biology, such as preparative extractions of plasmid DNA, centrifugation of plasmid DNA in caesium chloride gradient, agarose or acrylamide gel electrophoresis, [lacuna] phenol or phenol-chloroform, ethanol or isopropanol precipitation of DNA in saline medium, transformation in *Escherichia coli* and the like, are well known to persons skilled in the art and are widely described in the literature [Maniatis T. et al., "Molecular Cloning, a Laboratory Manual", Cold Spring Harbor Laboratory, Cold Spring Harbor, N.Y., 1982; Ausubel F. M. et al. (eds), "Current Protocols in Molecular Biology", John Wiley & Sons, New York, 1987].

The pBR322- and pUC- type plasmids and the phages of the M13 series are of commercial origin (Bethesda Research Laboratories).

For the ligations, the DNA fragments can be separated according to their size by agarose or acrylamide gel electrophoresis, extracted with phenol or with a phenol/chloroform mixture, precipitated with ethanol and then incubated in the presence of phage T4 DNA ligase (Biolabs) according to the recommendations of the supplier.

The filling of the protruding 5' ends can be performed with the Klenow fragment of *E. coli* DNA polymerase I (Biolabs) according to the specifications of the supplier. The destruction of the protruding 3' ends is performed in the presence of phage T4 DNA polymerase (Biolabs) used according to the recommendations of the manufacturer. The destruction of the protruding 5' ends is performed by a controlled treatment with S1 nuclease.

Site-directed mutagenesis in vitro by synthetic oligodeoxynucleotides can be performed according to the method developed by Taylor et al. [Nucleic Acids Res. 13 (1985) 8749–8764] using the kit distributed by Amersham.

The enzymatic amplification of the DNA fragments by the so-called PCR technique [Polymerase-catalyzed Chain Reaction, Saiki R. K. et al., Science 230 (1985) 1350–1354; Mullis K. B. and Faloona F. A., Meth. Enzym. 155 (1987) 335–350] can be performed using a DNA thermal cycler (Perkin Elmer Cetus) according to the specifications of the manufacturer.

The verification of the nucleotide sequences can be performed by the method developed by Sanger et al. [Proc. Natl. Acad. Sci. USA, 74 (1977) 5463–5467] using the kit distributed by Amersham.

EXAMPLES

Example 1

Construction of a Plasmid Carrying the β-Galactosidase Gene Inserted Between the ITRs of AAV2

This example describes the construction of a vector, designated pXL2373, carrying 2 ITR regions flanking a marker gene (βgal) and a polyadenylation site, serving as intermediate for the preparation, by recombination, of a recombinant adenovirus.

The plasmid pXL2373 (FIG. 2) contains especially a fragment comprising the LTR (long terminal repeat) of the Rous sarcoma virus (RSV), the *Escherichia coli* lacZ gene with the sequences for nuclear localization, and, the polyadenylation signals of the SV40 early region, the said fragment being inserted between two truncated ITR sequences from AAV2. The sequence of the ITRs used is represented in SEQ ID No. 1 and 2.

The vector pXL2373 also contains an adenovirus region permitting homologous recombination.

Figure 3A:
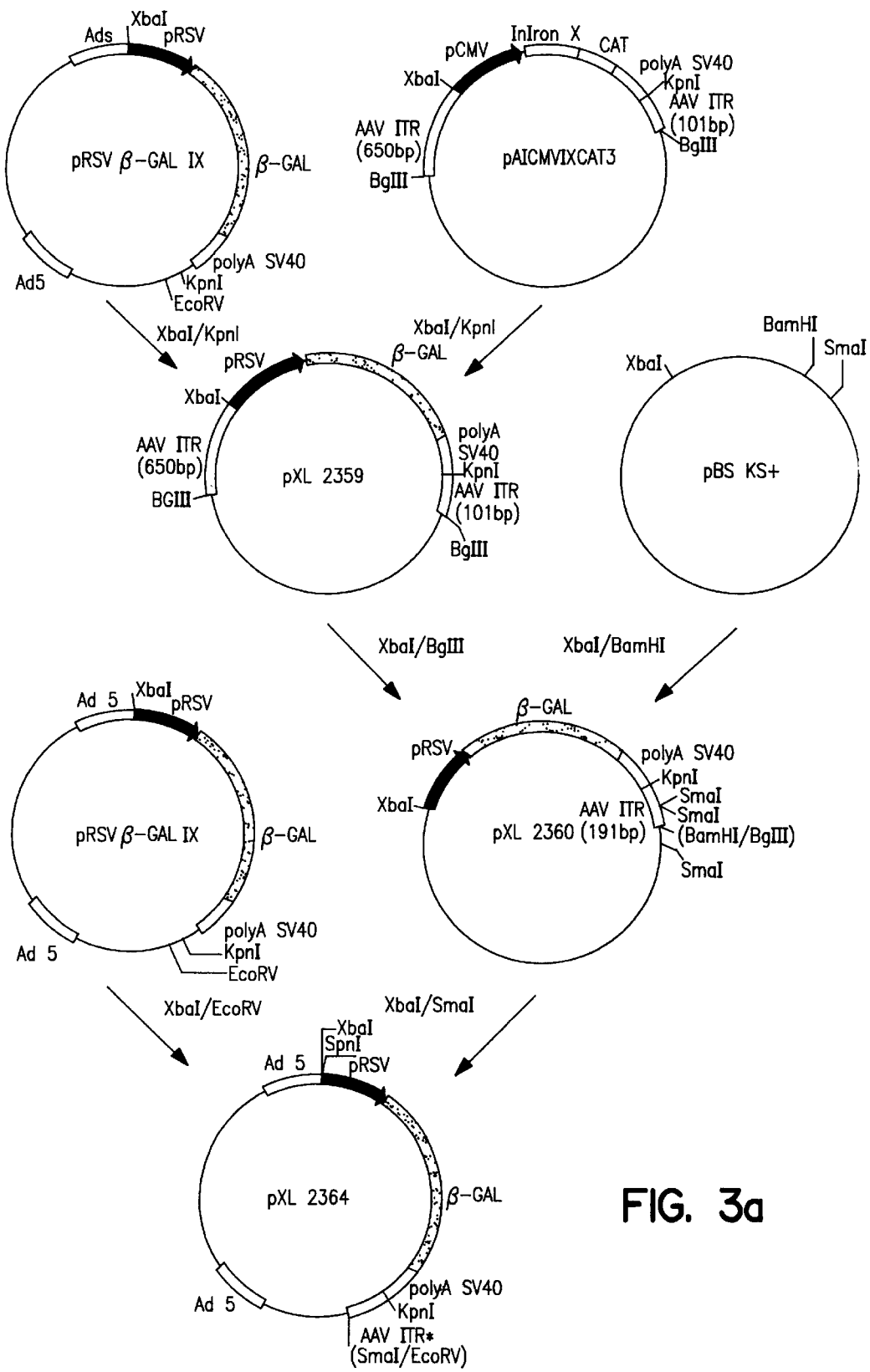
FIG. 3: Construction of the vector pXL2373

The vector pXL2373 was constructed in the following manner (FIG. 3): the DNA fragment carrying the LTR (long terminal repeat) of the Rous sarcoma virus (RSV), the *Escherichia coli* lacZ gene with the sequences for nuclear localization and the polyadenylation signals of the SV40 early region was isolated in the form of a XbaI-KpnI fragment from the plasmid pRSV-βgal (Stratford-Perricaudet et al., J. Clin. Invest. 90 (1992) 626). This fragment was then inserted at the corresponding sites of the plasmid pAICMVIXCAT.3 (Philip et al., Molecular and Cellular Biology, in press). This step makes it possible to insert this fragment between the first 650 and the last 191 base pairs (bp) of AAV2. The resultant plasmid was called pXL2359 (FIG. 3a).

The XbaI-BglII fragment of pXL2359, containing the Rous sarcoma virus (RSV) LTR, the *Escherichia coli* lacZ gene and the sequences for nuclear localization and the polyadenylation signals of the SV40 early region, as well as the last 191 bp of AAV, was inserted at the corresponding sites of pBS KS+, to generate the plasmid pXL2360. This subcloning makes it possible to isolate this same fragment in the form of a XbaI-SmaI fragment. The XbaI-SmaI fragment of pXL2360 was then inserted at the compatible XbaI-EcoRV sites of pRSV-βgal to give the vector pXL2364 (FIG. 3a).

Figure 3B:
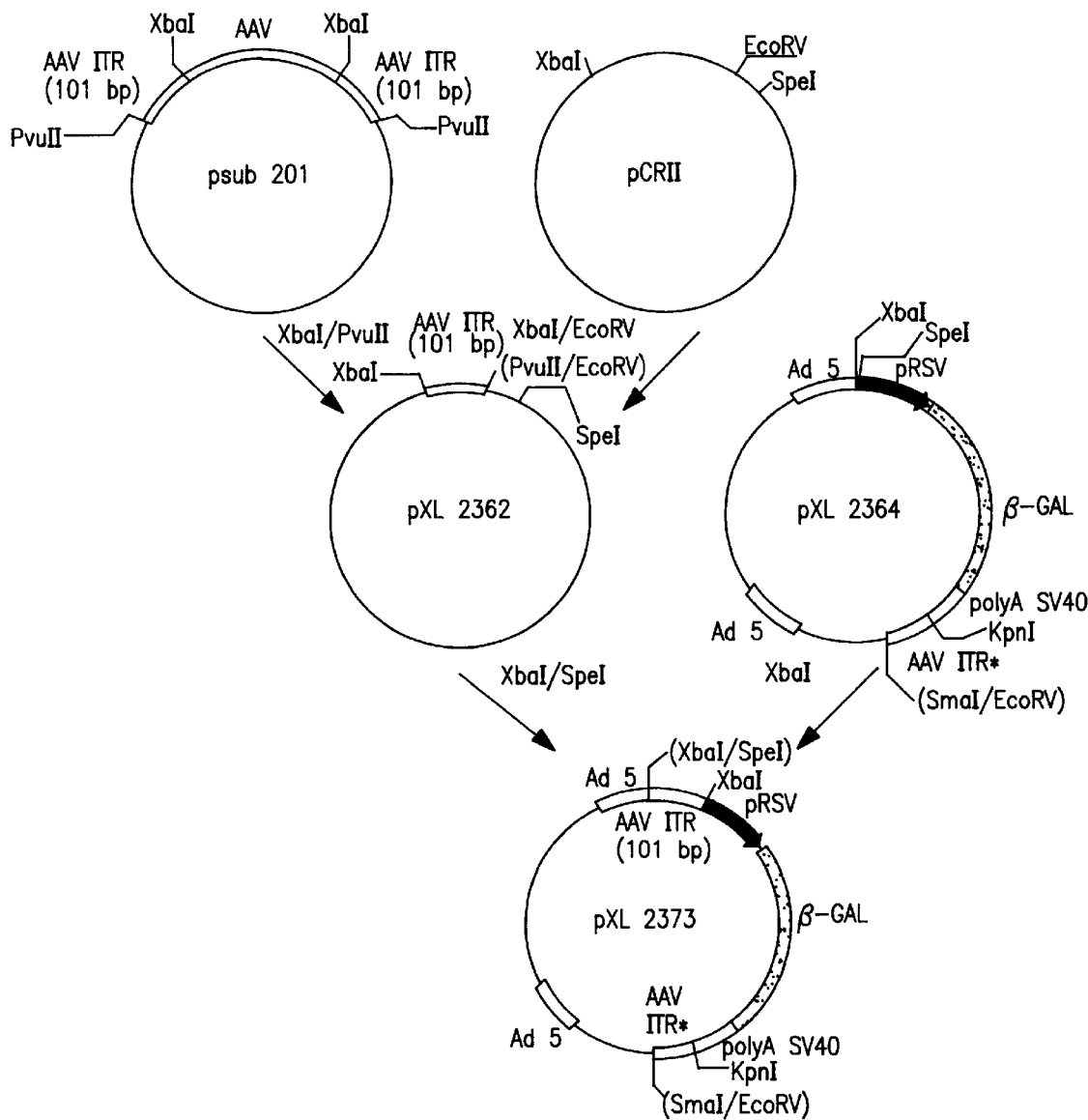

The plasmid psub201 has been described in Samulski et al. (J. Virol 61 (1987) 3096). The XbaI-PvuII fragment of this plasmid carrying sequences 4484 to 4675 from AAV was inserted at the XbaI-EcoRV sites of pCRII (Invitrogen) to generate the plasmid pXL2362. Finally, the SpeI-XbaI fragment of pXL2362 was introduced into the compatible XbaI site of pXL2364 (FIG. 3b).

The plasmid obtained was designated pXL2373 (FIG. 2). The capacity of this vector to allow the integration of the cassette is checked by transfection into the Hela and 293 cell lines.

Example 2

Construction of a Plasmid Carrying the β-Galactosidase Gene Inserted Between the AAV2 ITRs This example describes the construction of a vector, designated pXL2384, carrying 2 ITR regions flanking a marker gene (βgal) and a polyadenylation site, serving as intermediate for the preparation, by recombination, of a recombinant adenovirus.

The plasmid pXL2384 (FIG. 4) contains in particular a fragment comprising the LTR (long terminal repeat) of the Rous sarcoma virus (RSV), the *Escherichia coli* lacZ gene with the sequences for nuclear localization, and, the polyadenylation signals of the SV40 early region, the said fragment being inserted between two ITR sequences from AAV2. The sequence of the ITRs used is represented in SEQ ID No. 2 and 3.

The vector pXL2384 also contains an adenovirus region permitting homologous recombination.

The vector pXL2384 was obtained by inserting the following fragments:

the EcoRV-XhoI fragment of pRSVβgal carrying the part of the Ad5 protein IX serving for the recombination, and the EcoRV-KpnI fragment of pXL2360 (Example 1) carrying the 3' region of the lacZ gene from the EcoRV site, the polyadenylation signals of the SV40 early region, the ITR region from AAV plus the 47 bp situated upstream of the left ITR from AAV2, into the XhoI-KpnI sites of pXL2373 (Example 1).

Figure 4:
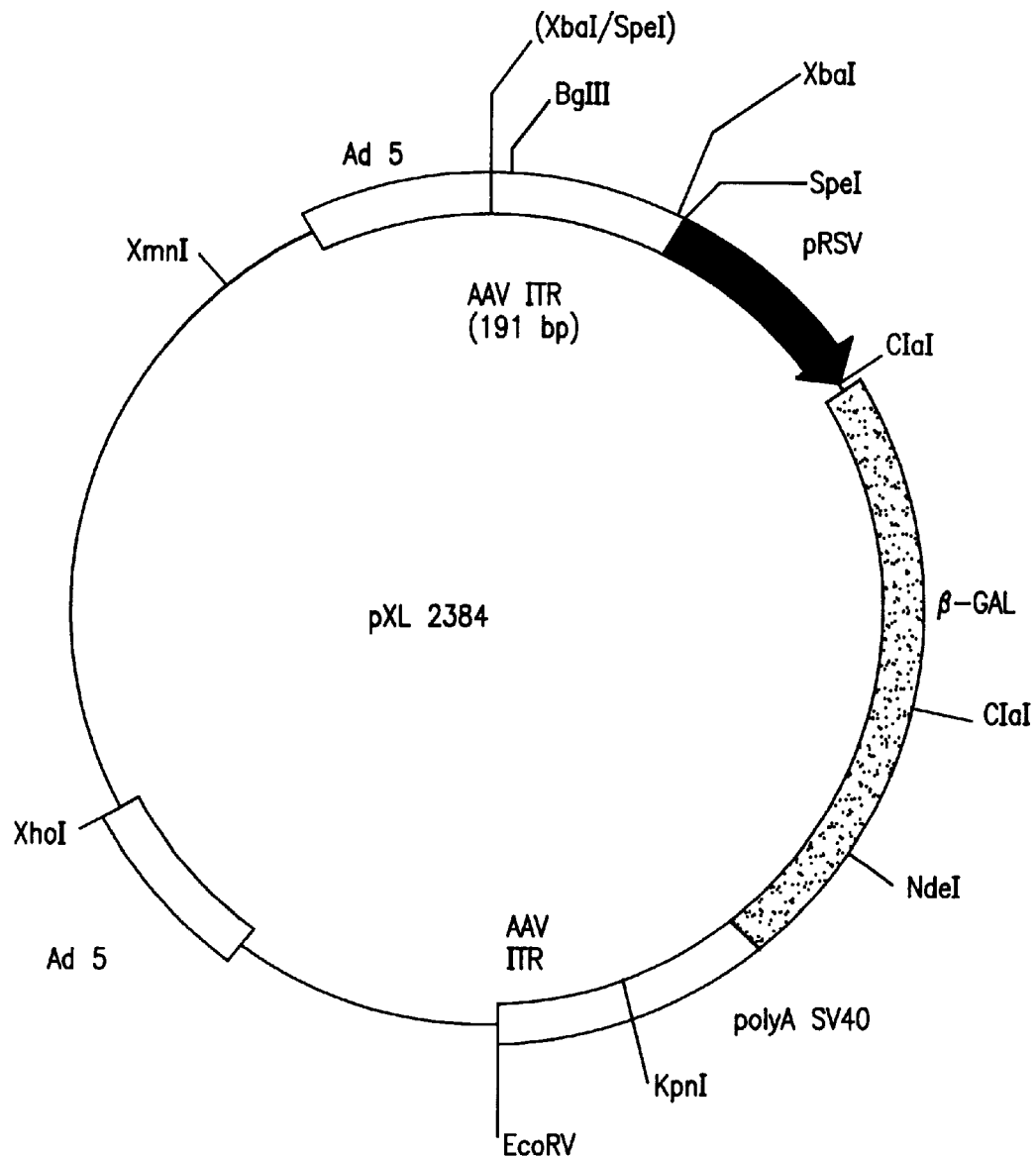
FIG. 4: Representation of the vector pXL2384

A map of this vector is given in FIG. 4. The capacity of this vector to allow the integration of the cassette is checked by transfection into Hela and 293 cell lines.

Example 3

Construction of a Plasmid Carrying the β-Galactosidase Gene Inserted Between the Strict ITRs from AAV2

In the plasmids described above, the ITR sequences used contain a 46 bp extension downstream of the left ITR or upstream of the right ITR, and/or a 9 pb deletion in 5' of the left ITR (see SEQ ID No. 1–3). This example describes the construction of a plasmid containing a gene of interest inserted between the strict ITRs from AAV2. More particularly, this example describes the construction of a vector, designated pITRFL, carrying 2 strict ITR regions flanking a marker gene (βgal) and a polyadenylation site, serving as intermediate for the preparation, by recombination, of a recombinant adenovirus.

The plasmid pITRFL (FIG. 6) contains in particular a fragment comprising:

the LTR (long terminal repeat) of the Rous sarcoma virus (RSV), the *Escherichia coli* lacZ gene with the sequences for nuclear localization, and the polyadenylation signals of the SV40 early region, the said fragment being inserted between two strict ITR sequences from AAV2. The ITR sequence used is represented in SEQ ID No. 4.

The vector pITRFL also contains an adenovirus region permitting homologous recombination.

The vector pITRFL was constructed in the following manner: the strict ITR sequence was constructed by means of the following oligodeoxynucleotides:

seq 4259: (SEQ ID No. 6)
5' CTA GAT TGG CCA CTC CCT CTC TGC GCG CTC GCT CGC TCA CTG AGG CCG GGC GAC CAA AGG TCG CCC GAC GCC A 3' seq 4260: (SEQ ID No. 7)
5' AGC TTG GCG TCG GGC GAC CTT TGG TCG CCC GGC CTC AGT GAG CGA GCG AGC GCG CAG AGA GGG AGT GGC CAA 3'T seq 4560: (SEQ ID No. 8)
5' AGC TTG ACG CCC GGG CTT TGC CCG GGC GGC CTC AGT GAG CGA GCG A 3' seq 4561: (SEQ ID No. 9)
5' GCG CGC TCG CTC GCT CAC TGA GGC CGC CCG GGC AAA GCC CGG GCG TCA 3' seq 4263: (SEQ ID No. 10)
5' GCG CGC AGA GAG GGA GTG GCC AAC TCC ATC ACT AGG GGT TCC TAC TAG TG 3' seq 4264: (SEQ ID No. 11)
5' GAT CCA CTA GTA GGA ACC CCT AGT GAT GGA GTT GGC CAC TCC CTC TCT 3'

Figure 5:
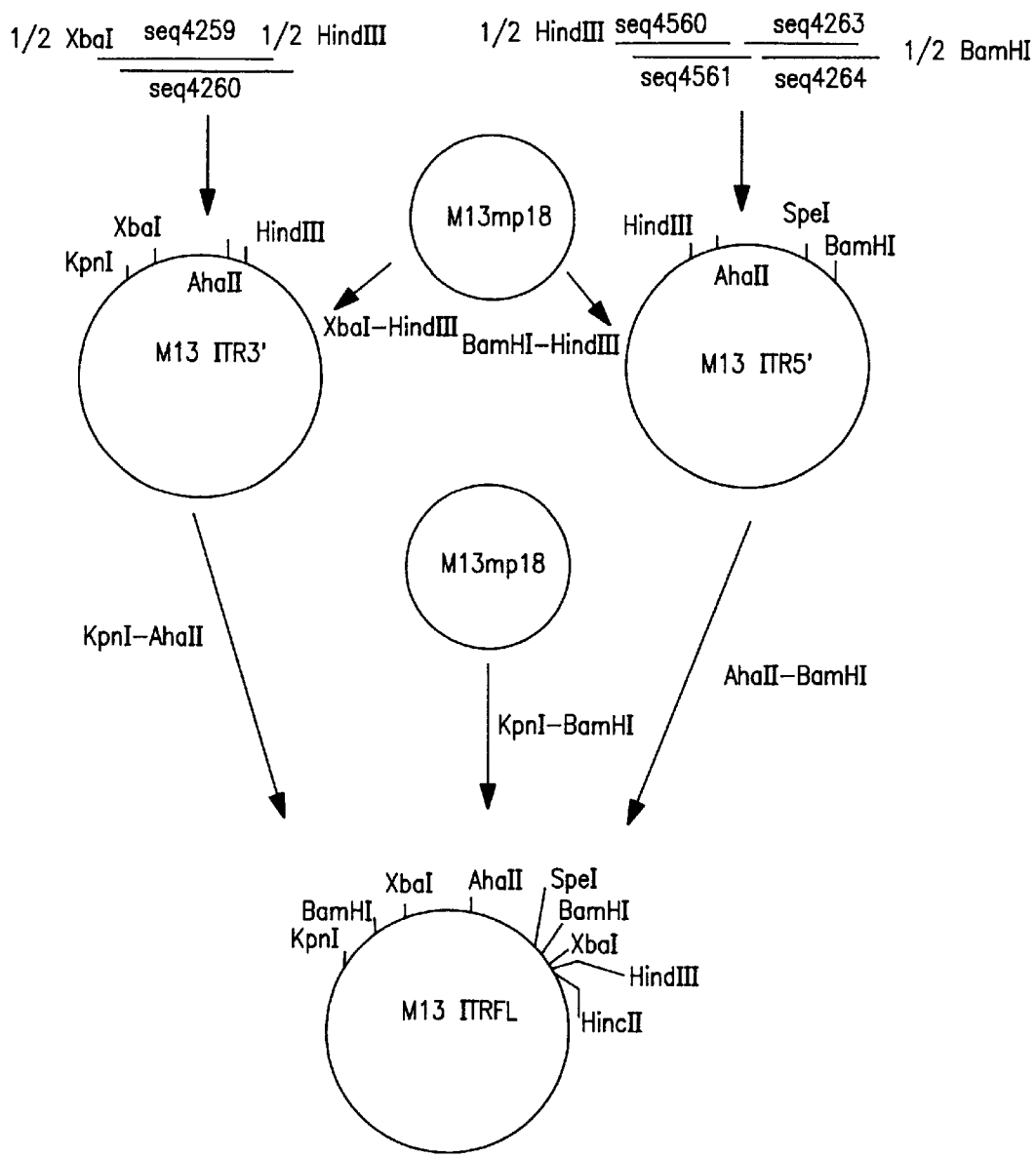
FIG. 5: Construction of the vector M13 ITR FL
Figure 6:
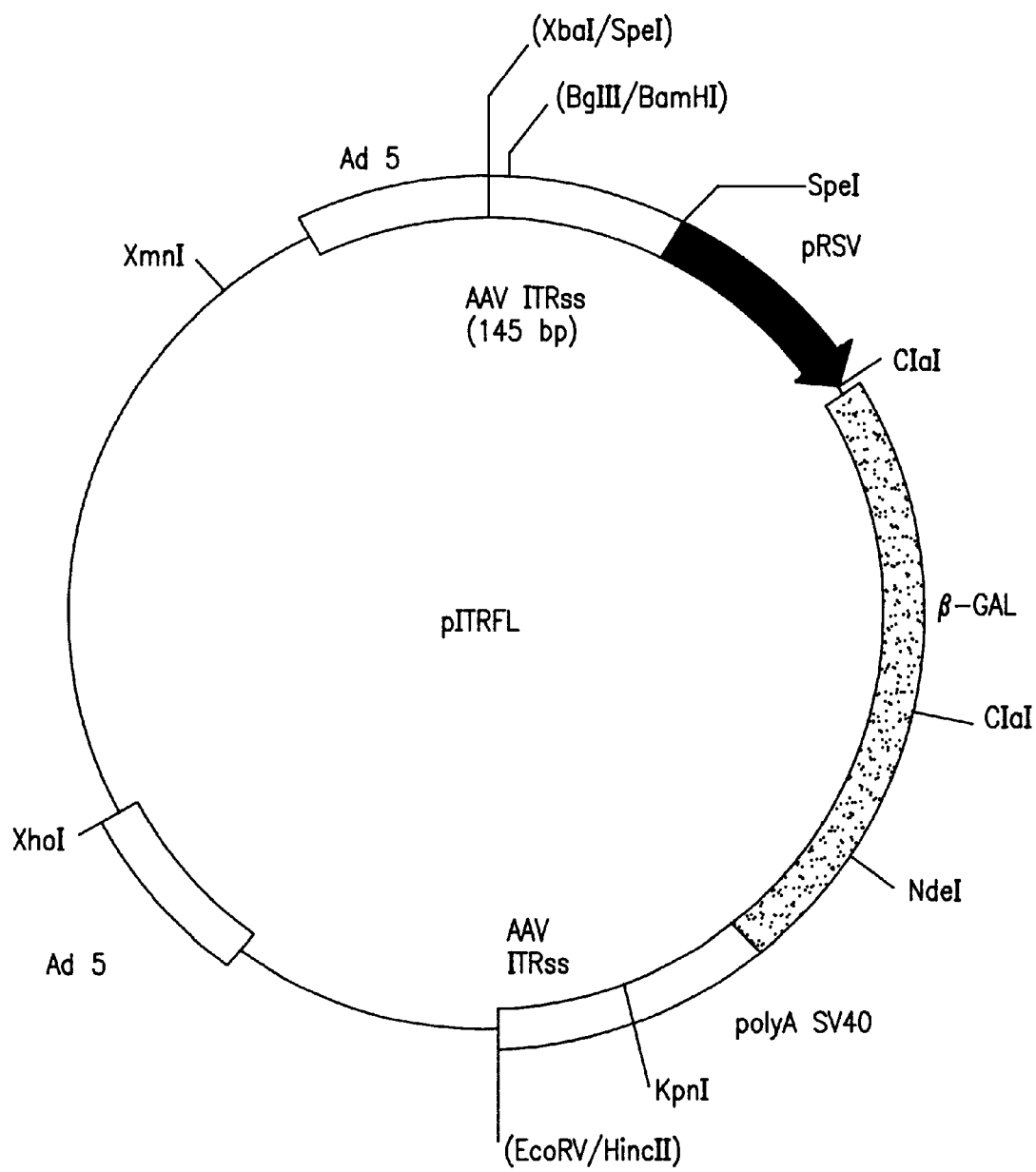
FIG. 6: Representation of the vector pITRFL

The oligodeoxynucleotides seq 4259 and seq 4260 are hybridized and form at their ends a semi-XbaI site and a semi-HindIII site (FIG. 5). These oligodeoxynucleotides are then introduced between the corresponding sites of M13mp18, and the bacteriophage obtained is called M13ITR5' (FIG. 5). The oligodeoxynucleotides seq 4560 and seq 4561 on the one hand and seq 4263 and seq 4264 on the other are hybridized in pairs and introduced between the HindIII and BamHI sites of M13mp18, the bacteriophage obtained is called M13ITR3'. The KpnI-AhaII fragment of M13ITR5' containing the 5' region of the AAV ITR up to the AhaII site (region 1 to 63 in the AAV sequence) and the AhaII-BamHI fragment containing the 3' region of the ITR (region 64 to 145) are introduced into the KpnI-BamHI sites of M13mp18 to give the vector M13"ITRFL". The BamHI-SpeI fragment of M13 "ITRFL" containing the entire sequence of the AAV ITR (bases 1 to 145) is introduced between the unique BglII-SpeI sites of pXL2384 to give the plasmid pRSVβgal ITR1ss plasmid. Finally, the KpnI-HincII fragment of M13 "ITRFL" containing the entire sequence of the AAV ITR (bases 1 to 145) and the EcoRV-XhoI fragment of pXL2384 carrying the Ad5 protein IX are introduced between the compatible XhoI-KpnI sites of pRSVβgalITR1ss to give pITRFL (FIG. 6).

Example 4

Construction of a Plasmid Carrying the β-Galactosidase Gene and the neoR Gene Inserted Between the ITRs from AAV2

This example describes the construction of a vector, designated pXL2388, carrying 2 ITR regions flanking 2 genes (βgal and neoR) and a polyadenylation site, serving as intermediate for the preparation, by recombination, of a recombinant adenovirus.

The plasmid pXL2388 (FIG. 7) contains in particular a fragment comprising:

the gene conferring the resistance to neomycin (neoR) under the control of the SV40 promoter, followed by the SV40 virus polyadenylation signals, the LTR (long terminal repeat) from the Rous sarcoma virus (RSV), the *Escherichia coli* lacZ gene with the sequences for nuclear localization, and, the polyadenylation signals of the SV40 early region, the said fragment being inserted between two ITR sequences from AAV2 (sequences represented on SEQ ID No. 2 and 3).

The vector pXL2388 also contains an adenovirus region permitting homologous recombination.

The vector pXL2388 was constructed in the following manner: the DNA fragment carrying the gene conferring the resistance to neomycin (neoR) under the control of the SV40 promoter, as well as the SV40 virus polyadenylation signals was isolated in the form of a BamHI fragment from the plasmid pMAMneoluc (Clontech). This fragment was then introduced into the BamHI site of the plasmid pBS KS+ (Stratagene) in order to introduce new restriction sites on either side of this fragment. The plasmid thus obtained is called pXL2363.

The DNA fragment carrying the gene conferring the resistance to neomycin (neoR) under the control of the SV40 promoter, as well as the SV40 virus polyadenylation signals was then isolated from pXL2363 in the form of an EcoRI-XbaI fragment and introduced into the EcoRI-XbaI sites of PCRII (Invitrogen) to give rise to the plasmid pXL2372.

Figure 7:
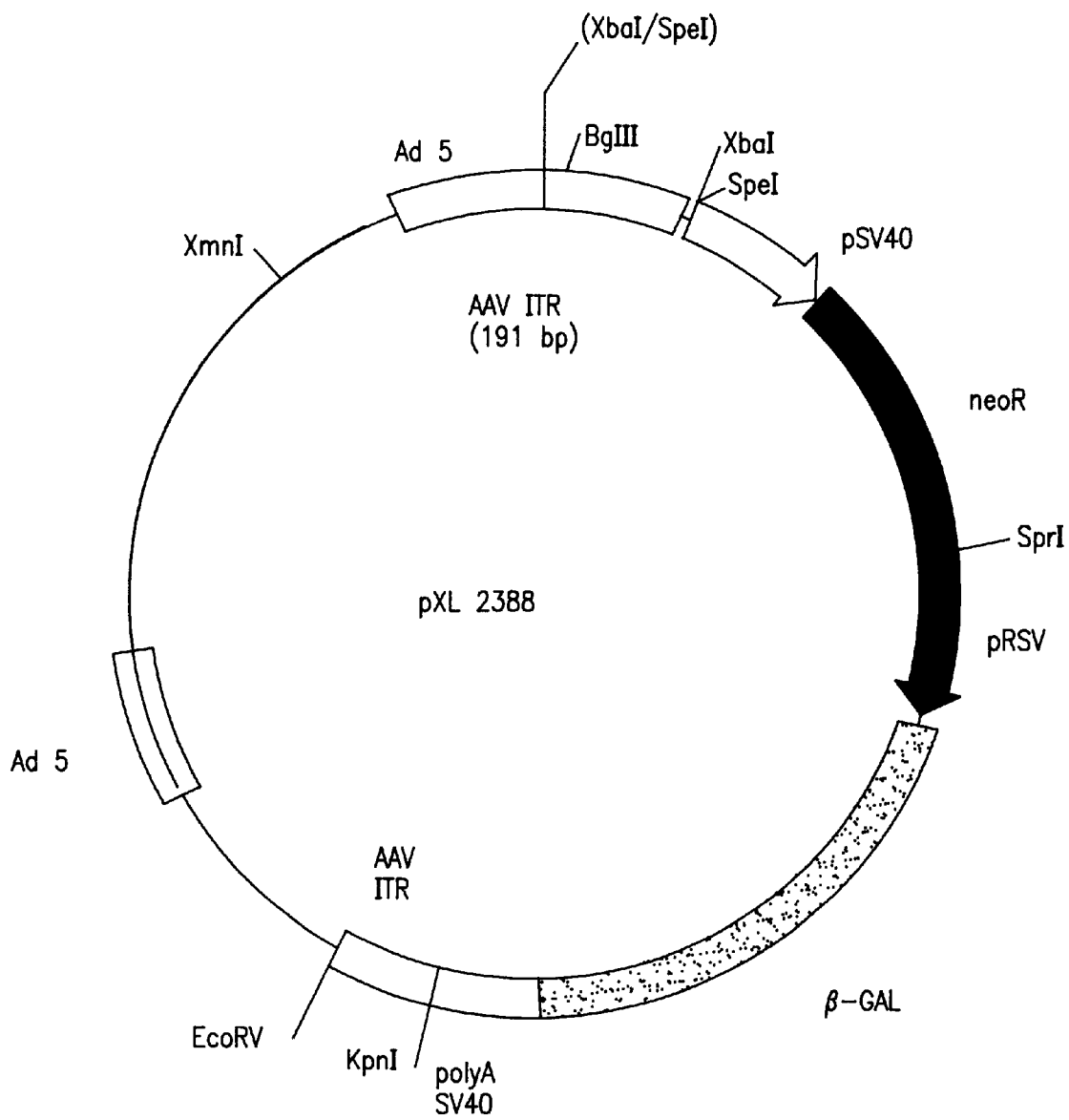
FIG. 7: Representation of the vector pXL2388

The DNA fragment carrying the gene conferring the resistance to neomycin (neoR) under the control of the SV40 promoter, as well as the SV40 virus polyadenylation signals was then isolated in the form of an SpeI fragment from pXL2372, and introduced into the SpeI site of pXL2384 (Example 2) to give rise to the plasmid pXL2388 (FIG. 7). A control plasmid, pXL2429, carrying the gene for resistance to neomycin under the control of the SV40 promoter and the lacZnls gene under the control of the RSV promoter which are inserted between the adenovirus sequences, but lacking the AAV ITR sequences, was also constructed. The sequence of the neomycin resistance gene under the control of the SV40 promoter is obtained from the SpeI-digested plasmid pXL2388, and this fragment was inserted into the SpeI site of pRSVGAIIX to give pXL2429.

The capacity of this vector to allow the integration of the cassette is checked by transfection to Hela and 293 cell lines. The cells 293 (2 $10^6$ cells cultured in 100 mm dishes) are transfected with the plasmids pXL2388 and pXL2429 according to the calcium phosphate technique. The day following the transfection, the medium is changed. After 72 hours, the cells are harvested and cultured after a 1/10 and a 1/50 dilution in a nonselective medium. 72 hours later, the medium is changed and a selective medium containing geneticin at 400 microg/ml is applied. Clones appear after about 2 weeks of culture in this medium and it is observed that the frequency of appearance of the clones is 100 times higher with the plasmid pXL2388 than with the plasmid pXL2429, reflecting the capacity of the ITRs to integrate the transgene into the cell genome.

Example 5

Construction of a Plasmid Carrying a Fusion Gene Sh ble::lacZ Inserted Between the AAV2 ITRs This example describes the construction of a vector, designated pXL2389, carrying 2 ITR regions flanking 1 fusion gene (Sh ble::lacZ), serving as intermediate for the preparation, by recombination, of a recombinant adenovirus.

The plasmid pXL2389 (FIG. 8) contains especially a fragment carrying, under the control of the SV40 promoter, a fusion between the gene for resistance to phleomycin (or to zeomycin) and the lacZ reporter gene, followed by SV40 virus polyadenylation signals, the said fragment being inserted between the sequences of two AAV ITRs (sequences represented on SEQ ID No. 2 and 3).

The vector pXL2389 also contains an adenovirus region permitting homologous recombination. The fusion carrying a dominant marker (Sh ble) and the lacZ reporter gene makes it possible to obtain a dominant phenotype associated with a rapidly identifiable phenotype (blue colour on X-gal) with a size not exceeding 3.5 kb. Because of this, the region inserted between the two AAV ITRs has a size not exceeding 4.3 kb.

Figure 8:
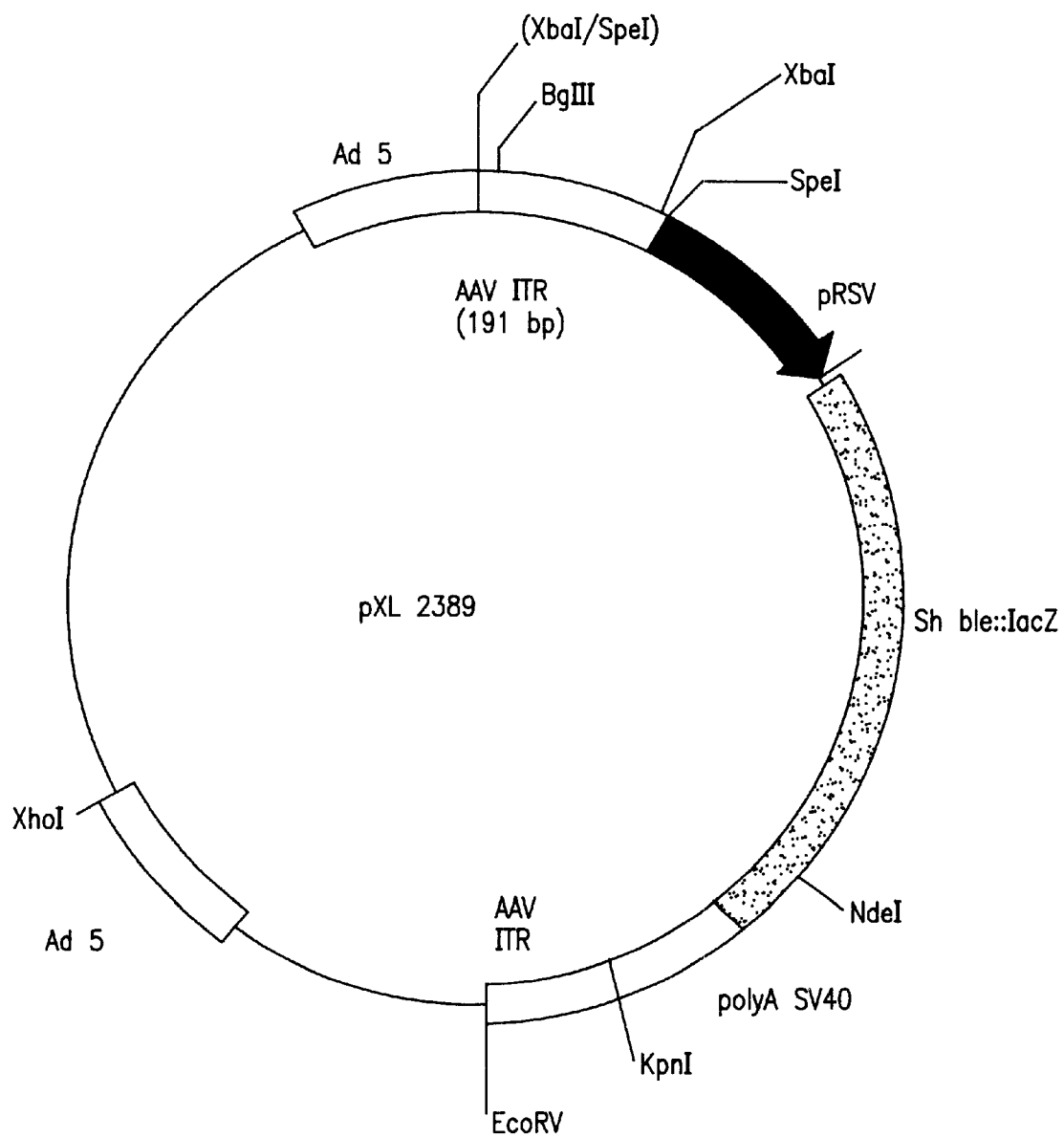
FIG. 8: Representation of the vector pXL2389

The vector pXL2389 was constructed in the following manner: the SpeI-NdeI fragment of the plasmid pUT593 (Cayla, Toulouse) carrying the SV40 promoter and the beginning of the Sh ble::lacZ fusion was isolated and then inserted between the SpeI-NdeI sites pXL2384 (Example 2). The plasmid thus obtained was designated pXL2389 (FIG. 8). The capacity of this vector to allow the integration of the cassette is checked by transfection into the Hela and 293 cell lines.

Example 6

Construction of a Plasmid Carrying the Apolipoprotein AI Gene Inserted Between the AAV2 ITRs Apolipoprotein AI is a protein consisting of 243 amino acids, synthesized in the form of a prepropeptide of 267 residues, having a molecular mass of 28,000 daltons. It is synthesized in man specifically in the liver and the intestine and it constitutes the essential protein of the HDL particles (70% of their mass as protein). It is abundant in plasma (1.0–1.2 g/l). Its best biochemically characterized activity is the activation of lecithin-cholesterol acyl-transferase (LCAT), but numerous other activities are attributed to it, such as especially the stimulation of the efflux of cellular cholesterol. The physiological role of apolipoprotein AI appears to be counterbalanced by apolipoprotein AII since, in man, the ratio of the two plasma concentrations (AII/AI) is very closely correlated with coronary risk. Apolipoprotein AI plays a major role in the resistance to atherosclerosis, probably linked to the reverse transport of cholesterol, since the only expression of this apolipoprotein in transgenic mice makes it possible to reduce 40-fold the surface area of the lipid deposits in the aorta compared with control mice (Rubin et al. 1993 Science, In Press). Its gene, 1863 bp long, has been cloned and sequenced (Sharpe et al., Nucleic Acids Res. 12(9) (1984) 3917). Moreover, various natural variants of apoAI have been described in the prior art.

Figure 9:
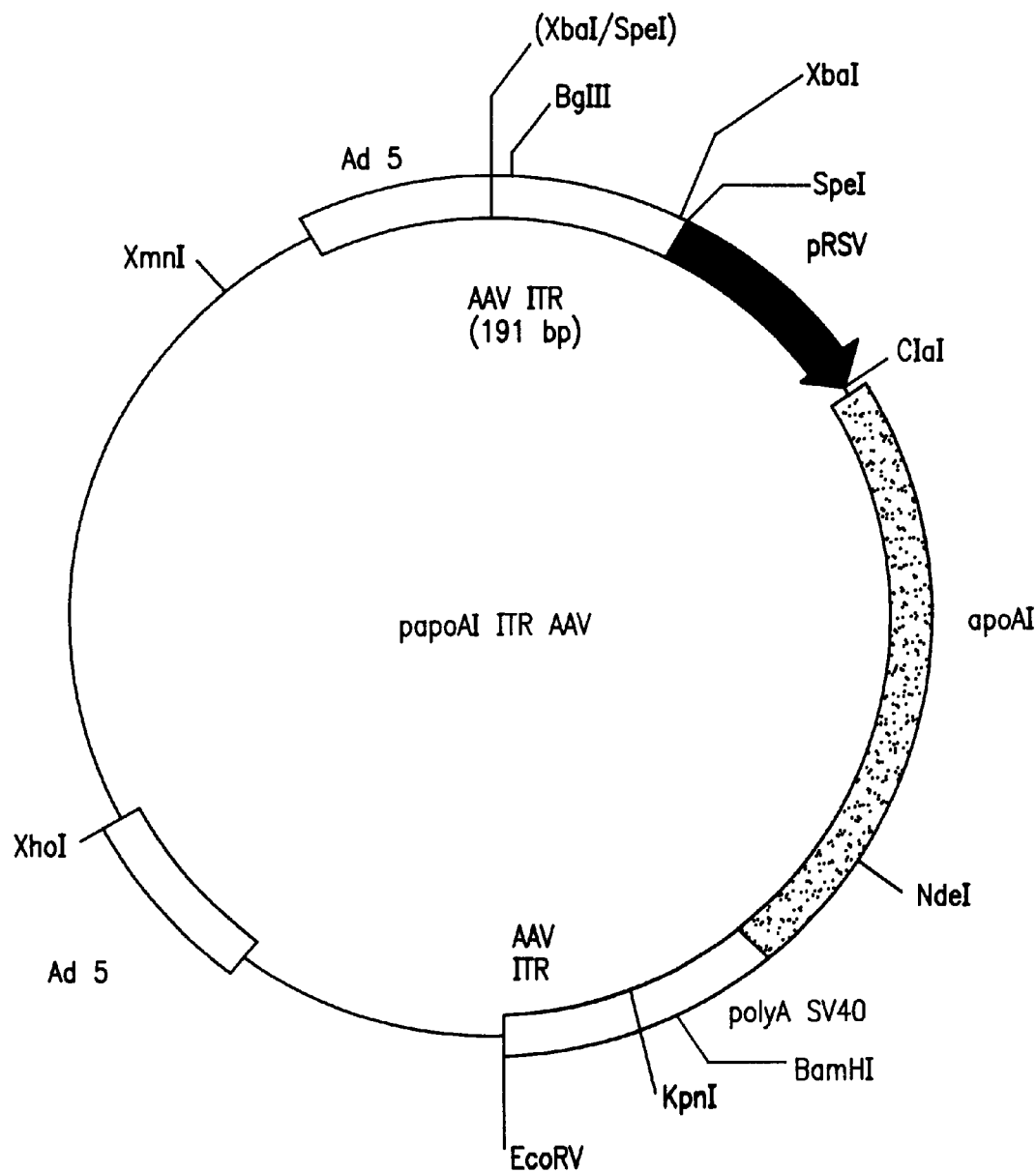
FIG. 9: Representation of the vector papoAI ITRAAV

The plasmids used to generate, by homologous recombination, the recombinant adenoviruses expressing the apoAI gene were constructed as follows:

Construction of the plasmid papoAI ITR AAV (FIG. 9):

The plasmid papoAI ITR AAV contains in particular the cDNA encoding preproapoAI under the control of the RSV promoter, the SV40 virus polyadenylation signals, the whole inserted between the AAV ITRs, as well as an adenovirus region permitting homologous recombination. It was constructed in the following manner: the DNA fragment carrying in particular the left ITR and the adenovirus 5 encapsulation sequence as well as the RSV virus LTR was isolated in the form of an XmnI-ClaI fragment of the plasmid pXL2384 (Example 2) and the DNA fragment carrying the cDNA encoding the preproapoAI and the SV40 virus polyadenylation signals was isolated in the form of a ClaI-BamHI fragment from the plasmid pXL2244 (FR93 05125). These two fragments were then inserted into the XmnI-BamHI sites of the plasmid pXL2384, to generate the plasmid papoAI ITR AAV. During this last step, the lacZ region, followed by the SV40 polyA, was removed.

The capacity of this vector to allow the integration of the cassette is checked by transfection into Hela and 293 cell lines.

Example 7

Construction of the Plasmid pXL2ϵ29

This example describes the construction of a vector pXL2629 carrying 2 ITR regions flanking the lacZ marker gene and a polyadenylation site, serving as intermediate for the preparation, by recombination, of a recombinant adenovirus. This plasmid differs from the plasmid pXL2384 by the left AAV ITR sequence (SEQ ID No. 5). The plasmid pXL2359 (Example 1) was digested with HinfI of which the end was made blunt by a bacteriophage T4 DNA polymerase treatment and then redigested with PstI; a fragment of about 200 bp carrying the AAV ITR (sequence figure) was isolated and introduced into the plasmid pBSKS+ at the PstI and SmaI sites (blunt end). The plasmid thus constructed is pXL2580. The plasmid pXL2581 is derived from pXL2384 by inserting 2 oligonucleotides seq 4674 and sep 4675 at the BglII-SpeI sites of pXL2384; this plasmid therefore carries, in place of the left AAV ITR of pXL2384, a unique BstBI site which could be used to construct recombinant adenoviruses AdITRsAAVRSVBgal by the technique for transfection of a ligation mixture of two linearized plasmids in the cells 293.

seq4674: 5'GATCTTTCGAAT3' (SEQ ID No. 12)
seq 4675: 5' CTAGATTCGAAA3' (SEQ ID No. 13)

The plasmid pXL2629 was constructed in the following manner: the plasmid pXL2580 was digested with BamHI-BglII and the fragment of about 170 bp, containing the complete AAV ITR sequence, was introduced into the plasmid pXL2581 previously linearized with BglII.

Example 8

Preparation of the Adenovirus Ad ITRsAAVRSVβGal

This example describes the construction of a defective recombinant adenovirus comprising a cassette allowing the integration of a gene into the genome of cells. More particularly, this adenovirus, designated Ad ITRsAAVRSVβGal, comprises a cassette composed of 2 AAV ITRs surrounding the βgal gene. This adenovirus was obtained by cotransfection of the plasmid pXL2384 for recombination with a deficient adenoviral vector, into the helper cells (line 293) providing in trans the functions encoded by the adenovirus E1 regions (E1A and E1B).

More precisely, the adenovirus Ad ITRsAAVRSVβgal was prepared by homologous recombination in vivo between the adenovirus AdRSVβGal (Stratford-Perricaudet et al., J. Clin. Invest. 90 (1992) 626) and the plasmid pXL2384 according to the following procedure: The plasmid pXL2384, linearized with the enzyme XmnI, and the adenovirus AdRSVβGal, linearized with ClaI, are cotransfected in the line 293 in the presence of calcium phosphate so as to allow the recombination. The recombinant adenoviruses thus generated are selected by plaque purification. After isolation, the recombinant adenovirus is amplified in the cell line 293, leading to a culture supernatant containing the unpurified recombinant defective adenovirus having a titre of about $10^{10}$ pfu/ml. For the purification, the viral particles are centrifuged on a caesium chloride gradient according to known techniques (see especially Graham et al., Virology 52 (1973) 456).

The adenovirus Ad ITRsAAVRSVβgal is preserved at −80° C. in 20% glycerol.

Example 9

Preparation of Adenovirus AdΔITRsAAVRSVβgal

This example describes the construction of a defective recombinant adenovirus containing a cassette permitting the integration of a gene into the genome of the cells. More particularly, this adenovirus, designated Ad ΔITRsAAVRSVβGal contains a cassette composed of 2 truncated AAV ITRs surrounding the βgal gene. This adenovirus was obtained by cotransfection of the plasmid pXL2373 for recombination with a deficient adenoviral vector, into the helper cells (293 line) providing in trans the functions encoded by the adenovirus E1 regions (E1A and E1B).

The procedure used is the same as that described in Example 7 for the preparation of the adenovirus Ad ITRsAAVRSVβgal. The adenovirus Ad ΔITRsAAVRSVβgal is preserved at −80° C. in 20% glycerol.

Example 10

Preparation of the Adenovirus Ad ITRFL

This example describes the construction of a defective recombinant adenovirus containing a cassette permitting the integration of a gene into the genome of the cells. More particularly, this adenovirus, designated Ad ITRFL, contains a cassette composed of 2 strict ITRs from AAV surrounding the βgal gene. This adenovirus was obtained by cotransfection of the plasmid pITRFL for recombination with a deficient adenoviral vector, into the helper cells (293 line) providing in trans the functions encoded by the adenovirus E1 regions (E1A and E1B).

The procedure used is the same as that described in Example 7 for the preparation of the adenovirus Ad ITRsAAVRSVβgal. The adenovirus AD ITRFL is preserved at −80° C. in 20% glycerol.

Example 11

Preparation of the Adenovirus Ad apoAIITRAAV

This example describes the construction of a defective recombinant adenovirus containing a cassette permitting the integration of a gene into the genome of the cells. More particularly, this adenovirus, designated Ad apoAI ITRAAV, contains a cassette composed of 2 truncated AAV ITRs surrounding the preproapoAI gene. This adenovirus was obtained by cotransfection of the plasmid papoAI ITR AAV for recombination with a deficient adenoviral vector, into the helper cells (293 line) providing in trans the functions encoded by the adenovirus E1 regions (E1A and E1B).

The procedure used is the same as that described in Example 8 for the preparation of the adenovirus Ad ITRsAAVRSVβgal. The adenovirus AD apoAI ITRAAV is preserved at −80° C. in 20% glycerol.

Example 12

Preparation of the Adenovirus Ad2629

This example describes the construction of a recombinant adenovirus Ad2629 carrying a cassette composed of 2 AAV ITRs surrounding the Bgal gene. This adenovirus was obtained by cotransfection of the plasmid pXL2629 with a deficient adenoviral vector, into the helper cells (line 293) providing in trans the functions encoded by the adenovirus E1 regions (E1A and E1B).

More specifically, the Ad2629 adenoviruses were prepared by homologous recombination in vivo between the adenovirus dl324 and the plasmid pXL2629 according to the following procedure: the plasmid pXL2629, linearized by XmnI, and the adenovirus dl324, linearized by ClaI, are cotransfected into the line 293 in the presence of calcium phosphate so as to allow the recombination. The recombinant adenoviruses thus generated are selected by plaque purification. After isolation, the recombinant adenovirus is amplified in the 293 cell line, yielding a culture supernatant containing the unpurified defective recombinant adenovirus having a titre of about 109–1010 pfu/ml. For the purification, the viral particles are centrifuged on a caesium chloride gradient according to known techniques (see especially Graham et al., Virology 52 (1973)456).

What is claimed is:

1. A defective recombinant adenovirus comprising a cassette capable of becoming integrated into the genome of an infected cell, wherein the cassette comprises a heterologous DNA sequence linked to an integration element, whereby the heterologous DNA and integration element integrate into the genome of the infected cell.

2. The adenovirus according to claim 1, wherein the AAV ITR is located upstream of the heterologous DNA sequence.

3. The adenovirus according to claim 1, wherein the heterologous DNA sequence is flanked by two AAV ITRs.

4. The adenovirus according to claim 1, wherein the ITR is an AAV-2 ITR.

5. The adenovirus according to claim 1, wherein the heterologous DNA sequence comprises a therapeutic gene.

6. The adenovirus according to claim 5, wherein the therapeutic gene is selected from the group consisting of a gene encoding an antigenic peptide and a gene encoding an antisense sequence.

7. The adenovirus according to claim 5, wherein the therapeutic gene encodes a protein product selected from the group consisting of an enzyme, a blood protein, a hormone, a lymphokine, a growth factor, a neurotransmitter, an apolipoprotein, a dystrophin, or a minidystrophin, the protein CFTR associated with cystic fibrosis, a tumor suppressor, a factor involved in coagulation, and a suicide gene.

8. The adenovirus according to claim 1, wherein the heterologous gene is under the control of a promoter.

9. The adenovirus according to claim 8, wherein the promoter is selected from the group consisting of a constitutive promoter, a regulated promoter, and a tissue-specific promoter.

10. The adenovirus according to claim 9, wherein the promoter is a viral promoter.

11. The adenovirus according to claim 10, wherein the promoter is selected from the group consisting of an E1A promoter, an MLP promoter, a CMV promoter, and an LTR-RSV promoter.

12. The adenovirus according to claim 1, wherein the cassette further comprises a marker gene linked to the integration element.

13. The adenovirus according to claim 12, wherein the marker gene is a β-galactosidase gene.

14. The adenovirus according to claim 1, which is free of at least the regions of its genome which are necessary for its replication in the target cell.

15. The adenovirus according to claim 14, which is an Ad5 or Ad2 type human adenovirus or CAV-2 type canine adenovirus.

16. A pharmaceutical composition comprising a defective recombinant adenoviruses according to claim 1 and a pharmaceutically acceptable vehicle.

17. The pharmaceutical composition according to claim 16, in injectable form.

18. The pharmaceutical composition according to claim 16, comprising between $10^4$ and $10^{14}$ pfu/ml of defective recombinant adenoviruses.

19. The pharmaceutical composition according to claim 18, comprising between $10^6$ to $10^{10}$ pfu/ml of defective recombinant adenoviruses.

20. A mammalian cell infected with an adenovirus according to claim 1.

21. The cell according to claim 20, which is a human cell in vitro.

22. The cell according to claim 20, which is a haematopoietic cell.

23. The cell according to claim 22, which is a CD34+ cell.

24. The cell according to claim 20, which is a tumor cell.

25. The adenovirus according to claim 3, further comprising an expression cassette for AAV rep and cap genes.

26. The adenovirus according to claim 25, which lacks adenoviral genes except the E4 region.

27. A method for the preparation of recombinant AAVs comprising introducing an adenovirus according to claim 3 into producing cells in vitro that express AAV rep and cap genes.

28. The method according to claim 27 wherein the producing cells are transfected with a plasmid carrying the rep and cap genes.

29. A method for the preparation of recombinant AAVs comprising coinfecting producing cells with an adenovirus according to claim 3 and with an adenovirus comprising AAV rep and cap genes.

30. The method according to claim 27, wherein the producing cells contain the rep and cap genes integrated into their genome.

31. The method according to claim 27, wherein the producing cells are 293 cells.

* * * * *